US005158872A

United States Patent [19]
Chavez et al.

[11] Patent Number: 5,158,872
[45] Date of Patent: Oct. 27, 1992

[54] AROMATIC SUBSTITUTED GLYCOSIDE

[75] Inventors: Rodrigo G. Chavez, LaJolla; Harold David, San Diego; Ernest K. Metzner, Del Mar; Gerald F. Sigler, San Diego; Emily S. Winn-Deen, Poway, all of Calif.

[73] Assignee: Hoechst Celanese Corporation, Somerville, N.J.

[21] Appl. No.: 565,092

[22] Filed: Aug. 10, 1990

Related U.S. Application Data

[60] Division of Ser. No. 91,861, Sep. 4, 1987, Pat. No. 4,963,479, which is a continuation-in-part of Ser. No. 916,262, Oct. 7, 1986, abandoned.

[51] Int. Cl.$^5$ .......... C12Q 1/40; C12Q 1/54; C12N 9/26
[52] U.S. Cl. .......... 435/22; 435/14; 435/201
[58] Field of Search .......... 435/22, 14, 201

[56] References Cited

U.S. PATENT DOCUMENTS

| | | | |
|---|---|---|---|
| 3,753,864 | 8/1973 | Babson | 195/103.5 R |
| 4,025,392 | 5/1977 | Dougherty | 195/99 |
| 4,102,747 | 7/1978 | Driscoll | 195/103.5 C |
| 4,145,527 | 3/1979 | Burns et al. | 536/4 |
| 4,225,672 | 9/1980 | Hall | 435/74 |
| 4,233,403 | 11/1980 | Menson et al. | 435/22 |
| 4,304,854 | 12/1981 | Nix | 435/14 |
| 4,321,364 | 3/1982 | McCleary | 436/18 |
| 4,343,897 | 8/1982 | Neumann et al. | 435/19 |
| 4,376,197 | 3/1983 | Wallenfels | 536/17.4 |
| 4,427,771 | 1/1984 | Misaki | 435/22 |
| 4,451,563 | 5/1984 | Kaufman | 435/21 |
| 4,505,756 | 3/1985 | Nix | 435/14 |
| 4,544,631 | 10/1985 | Rausher et al. | 435/14 |
| 4,683,198 | 7/1987 | Ishikawa | 435/22 |
| 4,963,479 | 10/1990 | Chavez et al. | 435/22 |

FOREIGN PATENT DOCUMENTS

| | | |
|---|---|---|
| 0157384 | 10/1985 | European Pat. Off. . |
| 2752501 | 5/1979 | Fed. Rep. of Germany . |
| 3301956 | 7/1984 | Fed. Rep. of Germany . |
| 3323245 | 1/1985 | Fed. Rep. of Germany . |
| 60-02199 | 1/1985 | Japan . |
| 0002199 | 1/1985 | Japan .......... 435/22 |

OTHER PUBLICATIONS

Myrbäck et al, (1950) in "The Enzymes", vol. 1, Part 1, pp. 691-694, Acad. Press, N.Y.
Hafkensheid et al. (1985) *J. Clin. Chem. Clin. Biochem.*, 23(9), 529-533, in *Chem. Abst.*, 103, p. 318, Abst. #174405w.

(List continued on next page.)

Primary Examiner—Douglas W. Robinson
Assistant Examiner—Jon P. Weber
Attorney, Agent, or Firm—Raymond R. Wittekind

[57] ABSTRACT

An aromatic substituted glycoside is disclosed of the formula $$\begin{array}{c} CH_2OH \\ \text{-O} \\ HO \quad OH \\ OH \end{array} \left[ \begin{array}{c} CH_2OH \\ \text{-O} \\ OH \\ OH \end{array} \right]_n \begin{array}{c} CH_2OH \\ \text{-O} \\ OH \\ OH \end{array} \text{-OR}$$

wherein the configuration of the substituted —OR on the anomeric carbon is alpha, n is an integer of 0 or 1, and R is a substituted aromatic radical selected from the group (a) $R_1$-substituted phenyl with $NO_2$ (b) $R_3, R_4, R_2$-substituted naphthyl (c) $R_6, R_5$-substituted naphthyl where $R_1$ through $R_6$ are independently halogen, $NO_2$, $SO_3H$, $$\underset{COR_7}{\overset{O}{\|}}, \quad \underset{-C-OH}{\overset{O}{\|}}, \quad \underset{-C-H}{\overset{O}{\|}}, \quad \underset{OCR_7}{\overset{O}{\|}},$$

where $R_7$ is lower alkyl; and includes its stereoisomers, optical isomers and geometric isomers and mixtures of the foregoing isomers. These substrates are useful as direct substrates for alpha-amylases. A process for the preparation of the substrates and related substances is also described.

6 Claims, No Drawings

OTHER PUBLICATIONS

Henkel et al, (Jan. 10, 1985) DE 3,323,245 in *Chem. Abst.* 102, p. 323, Abst. #108927w.

Tejima et al. (Feb. 8, 1986) JP 61,28,400 in *Chem. Abst.*, 104, p. 290, Abst. #221358r.

Winn–Deen et al. (1988) *Clin. Chem.*, 34(10), 2005–2008.

Derwent Publication 84-189754/31 of Offenlegungsschrift 33 01 956, published Jul. 26, 1984.

Dissertation—A. M. Fathy, Freiburg, 1984—Neue Substrate zur Bestimmung und Charakterisierung, Index IV-VIII, pp. 20, 103–111, 164–177, 187 and 188.

K. Wallenfels, et al., Carbohydrate Research, 61, 359 (1978).

K. Wallenfels, et al., Fresenius, Z. Anal. Chem., 301 169 (1980).

S. Teshima, et al., Clinica Chemica Acta, 150, 165 (1985).

E. Henkel, et al., J. Clin. Chem. Clin. Biochem., 22, 489 (1984).

A. P. Jansen and P. G. A. B. Wydeveld, Nature, 182, 525 (1958).

AROMATIC SUBSTITUTED GLYCOSIDE

This is a division of application Ser. No. 091,861 filed Sep. 4, 1987, U.S. Pat. No. 4,963,479 which is a continuation-in-part of application Ser. No. 916,262 filed Oct. 7, 1986.

BACKGROUND OF THE INVENTION

1. Field of the Invention

This invention relates to an aromatic substituted glycoside, and more particularly to such a glycoside which serves as a substrate for the direct determination of alpha-amylase. The present invention also relates to an improved method for the synthesis of the substrates as well as related glycosides.

2. Discussion of the Prior Art

One of the most widely studied and accepted procedures in clinical chemistry is the determination of serum and urine alpha-amylase which is used for the diagnosis of pancreatic disease.

During the past twenty-five years various amylase methods have been developed for use in the clinical laboratory. Some of the methods, i.e. saccharogenic method, involve complicated methodology which makes their routine use prohibitive. Other methods, i.e., turbidometric and viscosimetric methods for the determination of alpha-amylase activity, are dependent on changes in the physical properties of the substrate which may be influenced to a considerable degree by other factors present in the serum. Today, one of the most widely used methods for alpha-amylase determination is the starch-iodine method. With this method only a specific portion of the substrate is measured and the enzyme does not work under substrate saturation conditions Further, the presence of serum proteins could interfere with the starch-iodine reaction.

In addition to the above difficulties associated with the mentioned methods, a further difficulty is encountered because the aforementioned methods can be used to determine a rather limited range of alpha-amylase activity Also, some of the methods cannot be used for accurate determination of either sub-normal or highly elevated alpha-amylase levels Synthetic substrates comprising nitro aromatic glycosides have been employed in alpha-amylase determinations, such as reported in U.S. Pat. No. 4,145,527. The alpha-amylase acts preferentially on the endo bonds to form smaller fragments and therefore in order to get complete action to generate the chromophore, e.g. nitrophenol, an additional supporting enzyme must be employed.

The use of aromatic glycosides directly without the use of an additional supporting enzyme has been reported but the results achieved therewith have proved to be impractical because of poor kinetics and/or poor rate of color release.

The assay involving a synthetic substrate is reported. (Nature, 182 (1958) 525–526) in which a p-nitrophenol derivative of maltose is used. The p-nitrophenol replaces the anomeric hydroxyl group of maltose. Amylase causes cleavage of the substrate to produce p-nitrophenol which can be monitored at 410 nm. However, the assay is 16 hours long and maltase also cleaves the substrate. In this regard, Wallenfels, et al., Carbohydrate Research, 61, 359 (1978), also reported the use of 4-(p)-nitrophenyl-alpha-maltotriose as a direct assay substrate for pancreatic alpha-amylase. In addition, Wallenfels, et al, Fresenius Z. Anal. Chem., 301, 169 (1980), also reported the use of 2-(o)-nitrophenyl-alpha-maltotrioside. However these substrates also have proven impractical for use in a clinical assay for the reasons stated above. Wallenfels, et al., supra, 61, 359 (1978) also described the synthesis of a homologous mixture of p-nitrophenyl-alpha-maltooligosaccharides by enzymatic conversion employing alpha-cyclodextrin as the glucosyl donor, p-nitrophenyl-alpha-glucoside as the glucosyl acceptor and Klebsiella pneumoniae cycloglucanotransferase as the enzymatic agent. Similarly, L. M. Hall, U. S. Pat. No. 4,225,672, reports the preparation of aromatic substituted-alpha-maltooligosaccharides using cycloglucanotransferases from Bacillus strains. These methods yield mixtures of maltosides having typically 2 to 14, and at times more, glucose units in the polymeric chain, and thus require laborious separation techniques to obtain the desired maltosides and maltotriosides, generally in poor yield. To reduce the complexity of the mixture of maltooligosaccharides to one containing primarily lower maltooligosaccharide, such as, alpha-maltosides, maltotriside, and maltotetraosides, trimming enzymes of the phosphorylase class affecting the non-reducing termini of the polymers having multiple glucose units, i.e., those having, for example, five or more such units, have been employed (see, for example, Wallenfels, et al., Offenlegungsschrift 2 752 501). It has now been found that it is more efficient and cost effective, to trim the higher maltosides with enzymes of the amylase class to reduce the number of compounds of the cycloglucanotransferase mixture to a manageable level and thereby facilitate separation of the desired lower maltooligosaccharides, particularly to the nitrophenyl- and chloronitrophenylmaltoside and -maltotrioside The substrates and methods according to the present invention are distinguished from the known prior art by the combination that (1) additional supporting enzymes are not required to do the alpha-amylase analysis since the inventive substrates are acted upon by the alpha-amylase to directly cleave the substrate to generate the desired chromophore group; and (2) the kinetics are favorable, providing a useful rate of color release.

For example it has been found that 2-chloro-4-nitrophenyl-alpha-maltotrioside of the instant invention is hydrolyzed ten times faster than the prior art substrate, 4-nitrophenyl-alpha-maltotrioside under the optimum conditions for amylase assay. In addition, it has been found that the chromogens of the instant invention have improved spectral properties over monosubstituted nitrophenols in terms of higher molar extinction coefficients at the optimum pH for amylase assay. It has also been found that hydrazoic acid and alkali metal and alkaline earth salts thereof increase the rate of hydrolysis of the present maltooligosaccharides by alpha-amylase without effecting the molar extinction of the principal chromophore of the chromogenic moiety. Thus, sodium azide and lithium azide activate alpha-amylase and promote the enzyme induced hydrolysis of pancreatic and salivary alpha-amylase.

Furthermore, the method of the present invention is simpler and more accurate than the methods of the prior art.

SUMMARY OF THE INVENTION

The present invention is directed to an aromatic substituted glycoside, and more particularly to such a glycoside which serves as a substrate for the direct determination of alpha-amylase.

The aromatic substituted glycoside has the formula

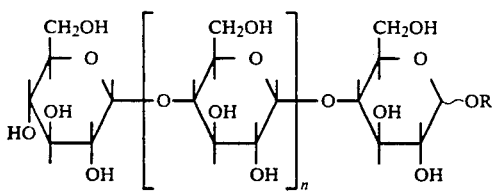
(I)

wherein the configuration of the substituted —OR group on the anomeric carbon is alpha-, n is an integer of 0 or 1 and R is a substituted aromatic radical selected from the group

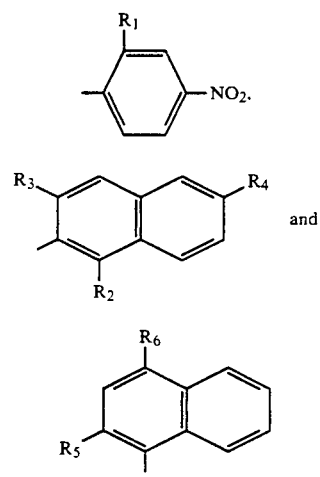

where $R_1$ through $R_6$ are independently halogen, $NO_2$, $SO_3H$,

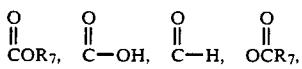

where $R_7$ is lower alkyl; and includes the stereoisomers, optical isomers and geometric isomers and mixtures of the foregoing isomers. The present invention is also directed to an enzymatic synthesis of the aforementioned substrates, as well as related substances, involving the homologation of substituted phenyl- or naphthyl-alpha-glucoside with a cyclodextrin by a cycloglucanotransterse, trimming of the non-reducing termini of the higher homologs with an amylase, and separation of the desired lower homologs.

DETAILED DESCRIPTION

The present invention is described primarily in terms of Compound I wherein n is 1 and R is

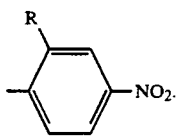

However, it will be understood that such description is exemplary only and is for purposes of exposition and not for purposes of limitation. It will readily be appreciated that the inventive concept described is equally applicable to the Compounds I having other n values and R substituents and the various stereo- and structural isomers.

In describing the glycoside I of the instant invention, the —OR substituent thereof is in the alpha- configuration.

As used herein, the term "halogen" includes a member of the halogen family selected from F, Cl, Br and I. The term "lower alkyl" refers to a monovalent substituent consisting of a straight or branched chain saturated hydrocarbon containing up to six carbon atoms, e.g. methyl, isopropyl, tertiary butyl, hexyl, etc.

In the preparation of the glycosides I of the invention, an anhydroide of formula II is selected,

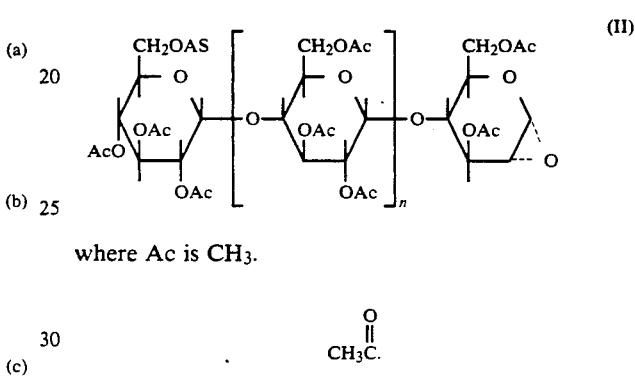
(II)

where Ac is $CH_3$.

$$\overset{O}{\underset{}{\overset{\|}{CH_3C.}}}$$

Such anhydro-compounds II can be prepared utilizing procedures as described below.

Such anhydro-derivatives (Compound II) are glucose extended analogs of 1,2-anhydro-alpha-D-glucopyranose triacetate, commonly known as Brigl's anhydride in the art (P. Brigl, Z. Physiol. Chem. 122, 245 (1922). The preparation of such derivatives is performed by similar chemistry as has been reported for Brigl's anhydride by R. Lemieux and J. Howard in "Methods in Carbohydrate Chem.", Vol II, Ed. Whistler and Wolfrom, p. 400 (1963). Accordingly, maltose or maltotriose is peracetylated with acetic anhydride in the presence of a catalyst such as, for example, sodium acetate, for 1 to 2 hours at 120°-140° C. The resultant peracetate with a beta-configuration at the anomeric carbon is heated with 3 to 10 equivalents of phosphorous pentachloride, with or without a small amount of supporting solvent. Preferably a chlorinated hydrocarbon such as carbon tetrachloride or chloroform is employed. A melt is obtained which is then heated at 70°-90° C. (reflux temperature) for 3 to 8 hours to give a 1-beta-chloro-2-trichloroacetyl derivative having the formula

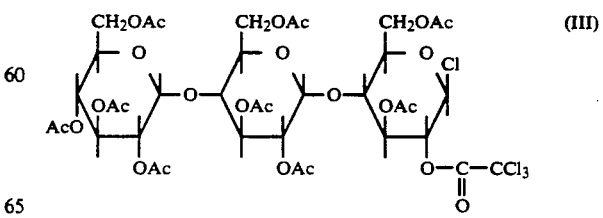
(III)

Compound III is selectively detrichloroacetylated to a 1-beta-chloro-2-hydroxy-derivative of the formula (IV) by treatment with saturated ammonia in diethylether for 10 minutes to 1 hour at 0°–10° C.

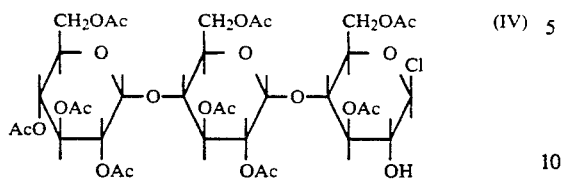
(IV)

Compound II is formed by treatment of Compound IV with a secondary amine, preferably diethylamine, or ammonia in an aromatic hydrocarbon, such as benzene or toluene, for a period of 8 to 24 hours at 15°–30° C.

Similar to Brigl's anhydride, the extended anhydrocompounds II react stereoselectively with the phenolic chromogens (ROH) in a refluxing aromatic hydrocarbon solvent such as toluene to give a high yield of the alpha-glycosides having the formula V in a manner similar to that reported by R. D. Guthrie in "The Carbohydrates", Vol. IA. Ed. Pigman and Horton, p. 424 (1972).

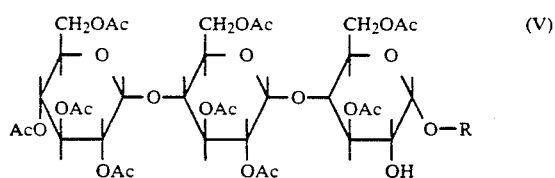
(V)

Typically, for the reaction, chromogen and the anhydro derivative IV are mixed in nearly equimolar concentrations and refluxed for 4 to 24 hours in toluene or benzene.

Compounds V are deacetylated by acidic or basic conditions well known in the art but preferably under acidic conditions which generally give less side-product formation associated with reactions at the glycosidic bond. In particular, mixtures of concentrated hydrochloric acid, an alcohol, and a chlorinated hydrocarbon such that the final concentration of acid is 1 M or less are found to give clean deacetylation. Thus, in a preferred mode, a mixture of 1 part concentrated hydrochloric acid, 10 parts methanol and 4 parts chloroform is reacted with Compound V for a period of 2 to 4 days at 20°–25° C. to yield Compound I.

Compound I is isolated by neutralization of the acid, removal of residual organic solvents and freeze-drying. Purification may be accomplished by a variety of methods well known in the art such as gel filtration, reverse phase high pressure liquid chromatography (HPLC) or partition chromatography In particular, partition chromatography on microcrystalline cellulose using mixed organic and aqueous solvent mixtures is found to be especially useful.

In the alternative, to prepare a maltooligosaccharide of Formula I wherein n is enlarged from 0 or 1 to 0 to 2, 2 and $R_1$ through $R_6$ are as above and, in addition, hydrogen, a phenyl- or naphthyl-alpha-glucoside of Formula VI

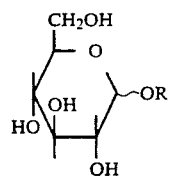
VI wherein the configuration of the substituent -OR on the anomeric carbon atom is alpha and R is as above is homolgated, i.e., transglycosylated, with a glucosyl donor in the presence of a cycloglucanotransferase to provide a mixture of alpha-maltooligosaccharides containing primarily the precursor glucoside VI and alpha-maltooligosaccharides of Formula I wherein the configuration of the substituent —OR on the anomeric carbon is alpha, R is as immediately above and n is predominantly 0 to 7 together with minor amounts of still higher maltooligosaccharides, followed by trimming the obtained mixture with an amylase to a less complex mixture containing primarily lower maltooligosaccharide, i.e., maltosides wherein n is 0 to 2, and separating the mixture of lower homologs obtained in the trimming process. The transglucosylation process is accomplished by conventional methods. For example, incubation of a glycoside acceptor of Formula VI, the preparation of which is described hereinbefore and which is further delineated in reviews such as A. F. Bahkov and G. E. Zaikov, "Chemistry of the O-Glycosidic Bond Formation and Cleavage," Pergamon Press, Oxford, England, 1979, with a glucosyl donor such as beta-cyclodextrin in the presence of cycloglucanotransferase such as Bacillus alkalophilic and a buffer such as sodium citrate/calcium chloride buffer yields typically a mixture of the starting glucside and alpha-maltooligosaccharides containing primarily 2 to 9 glucoside units, together with minor amounts of still higher alpha-maltooligosaccharides. The mixture of alpha-maltooligosaccharides so obtained may be isolated by conventional techniques such as precipitation, selective crystallization or chromatography, particularly high performance liquid chromatography. The trimming process may also be performed in situ. The latter process is preferred.

The trimming of the non-reducing termini of the mixture of alpha-maltooligosaccharides obtained in the transglycosylation process is effected by incubating the maltooligosaccharide mixture with an amylase in the presence of a buffer. The amylases may be of bacterial, fungal or mammalian origin and include alpha-amylases such as, for example, *Bacillus subtilus* alpha-amylase, *P. stutzeri* alpha-amylase or *Aspergillus oryzae* alpha-amylase, Aspergillus alpha-glucoamylase or rhyzopus alpha-amylase, or human salivary alpha-amylase or porcine pancreate alpha-amylase, respectively, or plant origin and include beta-amylases such as, for example, potato beta-amylase and malt beta-amylase. beta-Amylases are the preferred enzymatic trimmers. Potato and male beta-amylases are most preferred. While the concentration of the maltooligosaccharide mixture and the number of units of amylase employed in the trimming process is not narrowly critical, it is desirable to perform the trimming of the non-reducing termini of the mixture of aromatic-alpha-maltooligosaccharides at concentrations of the maltooligosaccharides within the range of about 0.05 to about 0.5 g/ml and units of amylase within the range of about 0.1 to 50 u/ml of reaction mixture A concentration of about 0.1 g/ml of mixed aromatic-alpha-maltooligosaccharide is preferred. Units of amylase are generally calculated in terms of saccharogenic activity, i.e., the amount of maltodioside liberated per unit time from soluble starch, or dextrinogenic activity, i.e., the amount of starch converted to dextrin per unit time.

The rate at which the higher alpha-maltooligosaccharides, e.g maltopenta- to -nonaosides of Formula I wherein n is 3 to 7, are trimmed at the non-reducing termini by amylases is markedly greater than the trimming rate for the lower alpha-maltosides of the transglycosylation process, e.g. the maltoside- to maltotetraosides of Formula I wherein n is 0 to 2. Thus, the time period during which the trimming process is to be performed is not critical. It has been found, however, that a convenient trimming time within the range of about 1 hour to 8 hours is obtained, i.e., the trimming is essentially complete, where the number of units of amylase is within the above range and the trimming temperature falls within the range of about 20° to about 50° C. A trimming temperature of about 25° C. is preferred. The course of the trimming process may be monitored by high performance liquid chromatography.

Buffers providing a pH range of from about 4 to about 8, a preferred pH range being from about 4.5 to about 6, may be employed in the trimming process. Among suitable buffers there may be mentioned alkali metal acetates and citrates, for examples, sodium or potassium acetate and citrate. Sodium acetate and citrate are preferred. Alternatively, the pH of the trimming process may be adjusted by titration.

The lower aromatic-substituted alpha-maltooligosaccharides, products of the trimming process, are isolated and separated by conventional methods For example, upon completion of the trimming reaction as, for example, indicated by high performance liquid chromatography monitoring, the reaction is terminated by the addition of a water miscible organic solvent, e.g., acetone to precipitate unreacted beta-cyclodextrin, salts, enzymes and free sugars, followed either by gel filtration or partition chromatography, preferably using high performance liquid chromatgraphy techniques.

The compounds I of the invention are useful as substrates for the direct determination of alpha-amylase without the need to use a supporting or auxiliary enzyme. The Compounds I are added to a sample e.g. serum, containing a quantity of alpha-amylase. The alpha-amylase reacts with Compound I whereby the —OR substituent is cleaved therefrom to form a chromophore which is spectroscopically identifiable and distinguishable from any unreacted glycoside and thus can be related to the quantity of alpha-amylase.

EXAMPLE 1

A. beta-Maltotriose hendecaacetate

Maltotriose, 15 g, was added portionwise with stirring to a 130° C. solution of 7.5 g sodium acetate in 75 ml acetic anhydride. The mixture was refluxed for 1 hour. The resultant solution was cooled to room temperature and poured into 600 ml of ice water. The suspension was stirred for one hour. The solid was filtered, washed with water and dried in vacuum over phosphorous pentoxide, to give 26.1 g of beta-maltotriose hendecaacetate.

B. 1-beta-Chloro-2-trichloroacetylmaltotriose nonaacetate beta-Maltotriose hendecaacetate, 3.0 g, was intimately mixed with 5.5 g of phosphorous pentachloride in a flask protected from moisture. Carbon tetrachloride, 5 ml, was then added and the solids were heated to obtain a fluid mixture. The solution was refluxed for 3 hours, then cooled to room temperature. The solution was rotary evaporated under vacuum to give an oil. The oil was dissolved in 200 ml ether and washed with three 200-ml portions of 1 M sodium carbonate. The ether layer was then dried over anhydrous magnesium sulfate, filtered and evaporated to give 3 g of crude solid product. The product was loaded on a column of Merck silica gel 60, 60 g, equilibrated with toluene. The product was eluted with 2:1 toluene/ethyl acetate, collecting 50 ml fractions. Fractions which were pure in the target component ($R_f$ 0.25) by thin layer chromatography (TLC) in 2:1 benzene/ethyl acetate were pooled and rotary evaporated to give a glassy solid. Trituration with petroleum ether gave 0.54 g of crystals of 1-beta-chloro-2-trichloroacetylmaltotriose nonaacetate, m.p. 129°–131° C.

C. 1-beta-Chloro-2-hydroxymaltotriose nonaacetate 1-beta-Chloro-2-trichloroacetylmaltotriose nonaacetate, 1.25 g, was dissolved in 25 ml of ether saturated with ammonia at 0° C. The mixture was stirred for 15 minutes at 0° C. during which time a colorless crystalline product precipitated. The product was filtered off and recrystallized from ethyl acetate/ether to give 0.34 g 1-beta-chloro-2-hydroxymaltotriose nonaacetate, m.p. 121°–130° C.

D. 1,2-Anhydro-alpha-D-maltotriose nonaacetate 1-beta-Chloro-2-hydroxymaltotriose nonaacetate, 200 mg, was dissolved in 15 ml of anhydrous benzene containing 35 ul of diethylamine The solution was stirred overnight (about 16 hours) at room temperature. The suspension was then filtered through a bed of about 1 g silica and the clear filtrate was rotary evaporated to an oil. The oil was dissolved in 20 ml of warm ether, the solution filtered from trace insoluble materials, and diluted with petroleum ether to first turbidity. Refrigeration gave a crystalline product which was collected and dried to yield 100 mg, of 1,2-anhydro-alpha-D-maltotriose nonaacetate, m.p. 158°–162° C.

EXAMPLE 2

2-Chloro-4-nitrophenyl-alpha-D-maltotrioside

2-Chloro-4-nitrophenol, 121 mg, and 1,2-anhydro-alpha-D-maltotriose nonaacetate, 500 mg, were dissolved together in 12 ml of toluene and the solution was refluxed for 16 hours. The toluene was rotary evaporated to an oily residue which was redissolved in ethyl acetate and extracted with four 20 ml portions of 0.5 M aqueous sodium bicarbonate, followed by two 20 ml-portions of saturated aqueous sodium chloride. The ethyl acetate layer was dried over anhydrous sodium sulfate, filtered and evaporated to an oil. The oil was redissolved in ether, 50 ml, and diluted with petroleum ether, 20 ml, to obtain a precipitate. After cooling to 4° C., the precipitate was collected and dried to yield 370 mg, of the desired alpha-glycoside nonaacetate of which 352 mg was dissolved in a mixture of 8 ml chloroform, 20 ml methanol, and 2 ml concentrated hydrochloric acid. The solution was stoppered and stirred at room temperature for 72 hours. The solution was then diluted with 25 ml water and the organic phase was separated. The aqueous phase was rotary evaporated on low vacuum to remove methanol. The aqueous acid solution was then treated batchwise with Dowex 50 (OH-form) until a pH of approximately 6.6 was reached. The resin was filtered and washed with water. The filtrate was lyophilized to give 175 mg of crude product. The product was purified by dissolving in a mixture of 2 ml water, 2 ml methanol and 12 ml acetone and loading on a column of 15 g of microcrystalline cellulose (FMC Avicel ®) equilibrated with acetone. The column was eluted in step gradients of acetone/water mixtures. Pure product was eluted between 8–12% water in acetone as monitored by analytical high pressure liquid chromatography (HPLC) on fractions (Econosphere TM C-8; 20% methanol/80% water; UV detection at 310 nm). The pooled fractions were rotary evaporated to remove acetone and the remaining aqueous solution was lyophilized to give a total of 33 mg of 2-chloro-4-nitrophenyl-alpha-D-maltotrioside.

EXAMPLE 3

4-Chloro-2-nitro-1-naphthyl-alpha-maltotrioside

4-Chloro-1-naphthol, 9 g, in 100 ml acetic acid was cooled to 15° C. and 3.25 ml concentrated nitric acid in 20 ml acetic acid was added dropwise over 15 minutes. After 1 hour, the reaction mixture was poured into 600 ml chilled water. The precipitate was filtered off, washed with water and dried to give a crude product. The product was partially purified by extracting with boiling hexane to obtain 3.5 g. Further purification was accomplished by dissolving in 10 ml chloroform, absorbing on 15 g silica and loading on a column of 90 g silica gel, equilibrated with hexane. The product was eluted with 5% ethyl acetate in hexane to give 0.8 g of 4-chloro-2-nitro-1-naphthol after evaporation, m.p. 142°–3° (d).

1,2-Anhydromaltotriose nonaacetate, 500 mg, and 4-chloro-2-nitrol-naphthol, 155 mg, were dissolved together in 12 ml toluene and the solution refluxed for 18 hours. The solution was cooled to room temperature and rotary evaporated to give a solid residue The residue was dissolved in ethyl acetate, 30 ml, and extracted four times with 0.5 M aqueous sodium carbonate (15 ml) followed twice by saturated aqueous sodium chloride (30 ml). The ethyl acetate phase was dried over anhydrous magnesium sulfate, filtered and evaporated to give a crude solid product. The product was dissolved in chloroform (20 ml), filtered from insolubles and the filtrate was mixed with 2 g silica gel and reevaporated to a powder. The silica with absorbed product was loaded on a column of 13 g Merck silica gel 60 equilibrated with n-hexane The column was eluted with chloroform followed by 4:1 chloroform/ethyl acetate. The product eluted in the latter mixture as monitored by TLC of the fractions. Appropriate fractions were concentrated and the product precipitated with hexane. Filtration and drying gave 234 mg of a powder of which 200 mg was dissolved in 10 ml of a 4:10:1 mixture of chloroform/methanol/concentrated hydrochloric acid, stoppered and stirred for 72 hours at room temperature. The solution was diluted with 25 ml water plus 25 ml chloroform and the phases separated. The aqueous phase was treated batchwise with Dowex 2 (OH⁻) resin until a pH of 3.8 was obtained. The suspension was filtered and the resin washed with 20 ml water. The filtrate was lyophilized to give 83 mg of crude product. For purification, crude product was dissolved in a mixture of 1 ml water, 1 ml methanol and 8 ml acetone. The solution was loaded on a column of 1 g microcrystalline cellulose (FMC Avicel ®) equilibrated with acetone. Elution with 90% acetone/10% water gave product which was concentrated and lyophilized to yield 15 mg of 4-chloro-2-nitro-1-naphthyl-alpha-maltotrioside.

EXAMPLE 4

2-Formyl-4-nitrophenyl-alpha-D-maltotrioside 100 mg of 2-Formyl-4-nitrophenol and 500 mg of 1,2-anhydromaltotriose nonaacetate were dissolved in 15 ml toluene and refluxed for 18 hours. The toluene was evaporated and the residue dissolved in ethyl acetate and washed four times with 50 ml portions of 10% aqueous sodium bicarbonate. The organic layer was dried over anhydrous sodium sulfate, filtered, and evaporated to a solid residue. The residue was crystallized from ether/ethyl acetate (50/0.5) by addition of hexane to give 270 mg of a product, m.p. 89°–104°C.

The resultant product (270 mg) was deacetylated by stirring in a solution of 6 ml chloroform, 15 ml methanol, and 1.5 ml concentrated hydrochloric acid. The reaction mixture was diluted with 50 ml water and the phases separated. The water phase was concentrated and neutralized to pH 6.9 by addition of Dowex 2 (OH⁻) resin. The suspension was filtered and the filtrate lyophilized to give 112 mg of crude product. The product was purified on a column of 2 g microcrystalline cellulose (FMC Avicel ®) in acetone/water gradients. Elution with 88% acetone/12% water gave a pool which was concentrated and lyophilized to yield 31 mg of 2-formyl-4-nitrophenyl-alpha-D-maltotrioside.

EXAMPLE 5

2-Chloro-4-nitrophenyl-alpha-D-glucoside 1,2-Anhydro-alpha-D-glucopyranose triacetate, 4.23 g, and 2-chloro-4-nitrophenol, 3.06 g, were dissolved in 350 ml of toluene. The solution was refluxed for 16 hours, cooled to room temperature and evaporated to a volume of 50 ml, at which point the product began to crystallize. The mixture was chilled to 0° C., and the crystals were collected on a filter, washed with cold toluene and hexane, and dried in vacuum to give 4.41 g (65% yield) of 2-chloro-4-nitrophenyl-alpha-D-glucoside 3,4,5-triacetate, mp 191°–195°. The glucoside was dissolved in 130 ml of a mixture of chloroform, methanol, and concentrated hydrochloric acid (4:10:1), then stirred at room temperature for 60 hours. The reaction mixture was diluted with 92 ml water, the layers were separated and the aqueous layer was extracted with 77 ml of chloroform. The aqueous layer was evaporated to a volume of 154 ml. The aqueous concentrate was loaded on a column of 96 ml Diaion HP-20 resin (Mitsubishi) equilibrated with water. The column was washed with about 1.5 l of water or until the pH of the effluent was about 6. The product was then eluted from the resin with 577 ml of methanol, collecting 6 equal fractions. Fractions 2–5 containing product (as indicated by High Performance Liquid Chromatography) were combined and evaporated to dryness to give 2.5 g (78%) of product which was approximately 94% pure by High Performance Liquid Chromatography (Alltech Econosphere C-8; 20% methanol/water; UV detection at $\lambda = 300$ nm).

EXAMPLE 6

Transfer of 2-Chloro-4-nitrophenyl-alpha-D-glucoside with Bacillus Cycloglucanotransferase 2-Chloro-4-nitrophenyl-alpha-D-glucoside, 0.32 g, and betacyclodextrin, 0.96 g, wee dissolved together in 9.6 ml of 0.05 M sodium citrate/0.005 M calcium chloride buffer, pH 5.0. Bacillus alkalophilic cycloglucanotransferase (Mitsubishi, 5.5 mg; 20,000 units/g wherein the units are defined in terms of the amount of soluble starch metabolized per unit time (see T. E. Barman, Enzyme Handbook, Vol. 1, Springer-Verlag, New York, N.Y. 1969, page 320), was then added and the mixture was stirred for 20 hours at room temperature, after which time High Performance Liquid Chromatography of the mixture (alltech Econosphere RP-8; 15% methanol/water; UV detection at $\lambda = 305$ nm) showed the following pattern: alpha-glucoside, 29.2%; alpha-maltoside, 15.3%; alpha-maltotrioside, 12.1%; alpha-maltoside, alpha-maltopentaoside, 8.4%; alpha-maltohexaoside, 9.0%; alpha-maltoheptaoside, 3.5%; alpha-maltooctaoside, 2.5%; alpha-maltononaoside and higher, 6.0%.

EXAMPLE 7

Trimming of 2-Chloro-4-Nitrophenyl-alpha-Maltodextrins with Sweet Potato beta-Amylase 2-Chloro-4-nitrophenyl-alpha-maltodextrin mixture, 9.6 ml, generated as in Example 6, was treated with 0.01 ml of an ammonium sulfate suspension of sweet potato beta-amylase (Behring Diagnostics, 10,000 units/ml; 1 unit being the amount of enzyme that produces 1.0 umole of maltase per minute from starch at 37°) for five hours at room temperature in 0.05 M sodium citrate/0.005 M calcium chloride buffer (pH 5.0). At this time, High Performance Liquid Chromatography of the mixture, as in Example 6, showed the following composition: alpha-glucoside, 31.9; alpha-maltoside, 19.9%; alpha-maltotrioside, 30.1%; alpha-maltotetraoside, 13.1%; and higher alpha-maltodextrins, 2.1%.

EXAMPLE 8

Transfer of 4-Nitrophenyl-alpha-D-glucoside with Bacillus Cycloglucanotransferase 4-Nitrophenyl-alpha-D-glucoside, 0.5 g, and betacyclodextrin, 5.0 g, were dissolved in 10 ml of 5 mM aqueous calcium chloride. Bacillus alkalophilic cycloglucanotransferase (20 mg) was added and the mixture was incubated for 18 hours at 40° C. High Performance Liquid Chromatography of a sample of the mixture (Unimetrics Lichrosorb RP-8; 15methanol/water; UV detector $\lambda = 305$ nm) showed the following composition: alpha-glucoside, 7.6%; alpha-maltoside, 7.7%, alpha-maltotrioside, 6.9% alpha-malto-tetraoside, 9.3%; alpha-maltopentaoside, 8.6% alpha-maltohexaoside, 7.5%; alpha-maltoheptaoside, 5.8% alpha-maltooctaoside, 5.3% alpha-maltononaoside and higher, 38.0%.

EXAMPLE 9

Trimming of 4-Nitrophenyl-alpha-maltodextrins with Bacillus subtitlus alpha-Amylase The mixture of 4-nitrophenyl-alpha-maltodextrins, 1 ml, from Example 8, was treated with 0.1 l mg Bacillus subtilus alpha-amylase (Behring Diagnostics, 1,800 U per mg; 1 unit being defined in terms of the starch liquefying ability of the enzyme per minute as measured with iodine) for one hour at 40° C. The mixture was assayed by High Performance Liquid Chromatography using the system as described in Example 6 and found to have the following composition: alpha-glucoside, 11.9%; alpha-maltoside, 23.8%; alpha-maltotrioside, 28.9%; alpha-maltotetraoside, 13.4%; alpha-maltopentaoside, 1.6% alpha-maltohexaoside, 10.0%; alpha-maltoheptaoside, 5.5%; alpha-maltooctaoside and higher, not detectable.

EXAMPLE 10

Trimming of 4-Nitrophenyl-alpha-maltodextrins with *Aspergillus oryzae* alpha-Amylase The mixture of 4-nitrophenyl-alpha-maltodextrins, 1 ml, from Example 8 was treated with Aspergillus oryzae alpha-amylase, 0.1 mg (Amano ATE 120 U/mg; 1 unit is defined as the amount of enzyme that dextrinizes 1 mg of starch (soluble) per minute at 37° at pH 5.5) at pH 4.5 for one hour at 10° C. The mixture was assayed by High Performance Liquid Chromatography using the system described in Example 6 and found to have the following composition: alpha-glucoside, 8%; alpha-maltoside, 29%; alpha-maltotrioside, 24%; alpha-maltotetraosie, 21%; alpha-maltopentaoside, 7%; alpha-maltohexaoside, 4%; alpha-maltoheptaoside, 2%; alpha-maltooctaoside and higher, not detectable.

EXAMPLE 11

Trimming of 2-Chloro-4-nitrophenyl-alpha-Maltodextrins with Malt beta-Amylase

A mixture of 2-chloro-4-nitrophenyl-alpha-maltodextrins was generated, as in Example 6, from 92.2 g alpha-glucoside, 333 g beta-cyclodextrin and 1.2 g of *Bacillus alkalophilic* cycloglucanotransferase reacted 68 hours at room temperature in 3.3 l of 0.05 M sodium citrate/0.005 M calcium chloride, pH 5.0. At this time, High Performance Liquid Chromatography showed the following mixture: alpha-glucoside, 18.1%; alpha-maltoside, 14.4%; alpha-maltotrioside, 12.15%; alpha-maltotetraoside, 11.1%; alpha-maltopentaoside, 8.3%; alpha-maltohexaoside, 6.2%; alpha-maltoheptaoside, 4.9%; alpha-maltooctaoside and higher, 18.4% beta-Amylase from malt (Amano; 1 unit being the amount of enzyme that will produce 1.0 uml of maltase per minute from soluble starch at 37°), 1.0 g (4,000 U), was then added and the reaction was stirred for two hours. High Performance Liquid Chromatography at this time showed the following distribution; alpha-glucoside, 22.1%; alpha-maltoside, 23.5%; alpha-maltotrioside, 34.0%; and alpha-maltotetraoside, 20%.

EXAMPLE 12

Isolation of 2-Chloro-4-nitrophenyl-alpha-maltotrioside from beta-Anylase Trimmed Maltodextrin Mixture A trimmed maltodextrin mixture generated as in Example 11, was diluted with 13.3 l acetone. The resultant suspension was refrigerated for three days, then filtered. The filter cake was washed with 500 ml 80% acetone/20% water and the combined filtrate was evaporated to a volume of 2 l. The concentrate was extracted four times with 2.5 l ethyl acetate/n-butanol (85:15). The aqueous solution, which was enriched in maltotrioside and maltotetraoside, was concentrated and lyophilized. The lyophilized product was redissolved in 200 ml methanol/water (5:2) and loaded on a mixed-column of micro-crystalline cellulose (Avicel ® FMC Corp.), 3 kg, and 1 kg woodflock equilibrated with acetone. The column was eluted sequentially with 48 l 100% acetone, 124 l 95% acetone/5% water, and 84 l 90% acetone/10% water, collecting 6–12 l fractions The alpha-maltotrioside was eluted primarily in the 90/10 fractions. These fractions were evaporated to remove acetone and the remaining aqueous concentrate was lyophilized to give 43.6 g of product which was homogeneous by High Performance Liquid Chromatography.

EXAMPLE 13

Trimming of 2-Chloro-4-nitrophenyl-alpha-maltodextrins with *Bacillus subtillus* alpha-Amylase 2-Chloro-4-nitrophenyl-alpha-maltodextrin mixture generated as in Example 6,was treated with 1.175 U of *Bacillus subtilus* alpha-amylase (Behring Diagnostics) over five hours at room temperature in 0.05 M sodium acetate/0.005 M calcium chloride buffer, pH 5.0. High Performance Liquid Chromatography of the mixture after this period showed the following composition: alpha-glucoside, 30.8%; alpha-maltoside, 20.8%; alpha-maltotrioside, 30.4%; alpha-maltotetraoside, 8.7%; alpha-maltopentaoside, 6.2%; alpha-maltohexaoside, 3.0%; alpha-maltoheptaoside and higher, not detectable.

EXAMPLE 14

Amylase assay with 2-Chloro-4-nitrophenyl-alpha-D-maltotrioside

The assay system consisted of 0.055 molar 2-(N-morpholino)-ethanesulfonic acid (MES1 buffer, pH=6.0, containing 51 millimoles/L of sodium chloride, 5 millimoles/L of calcium acetate and 4.44 millimoles/L of 2-chloro-4-nitrophenyl-alphamaltotrioside. The pH of the buffer was achieved by mixing the sodium salt and the free acid of MES.

The change in absorbance was monitored at 405 nm during the linear interval of 0.5 min to 6.0 min Gilford spectrophotometer and the incubation temperature was 37° C. Using a sample to reagent ratio of 1:60, a control serum containing 428 Units/L (based on Pantrak ® Amylase Test) of pancreatic amylase generated a $\Delta A$/minute of 0.029. A different control serum containing 455 Units/L (based on Pantrak Amylase Test) of salivary amylase generated a $\Delta A$/minute of 0.018.

Following the above procedure and employing, in addition, sodium azide at a concentration of 152 millimoles/liter, it was determined that 2-chloro-4-nitrophenyl-alpha-maltotrioside is hydrolyzed faster by pancreatic alpha-amylase (3-fold) and salivary alpha-amylase (6-fold) in the presence of sodium azide than in the absence of the salt. Under similar conditions, the rate of 2-chloro-4-nitrophenyl-α-maltotrioside hydrolysis by either pancreatic or salivary alpha-amylase is increased by lithium azide in the same manner as by sodium azide.

Likewise, following the above procedure, it was found that 230 millimoles of sodium azide increases the rate of substrate hydrolysis by pancreatic alpha-amylase and salivary alpha-amylase by 3.4- and 7.1-fold, respectively. Reducing the level of sodium azide in the system causes a reduction in the rate of 2-chloro-4-nitrophenyl-alpha-maltotrioside hydrolysis by the alpha-amylase isoenzymes. The rate reduction due to the decrease in concentration of the sodium azide is not equal and is specific for each isoenzyme. The rate of 2-chloro-4-nitrophenyl-alphamaltotrioside hydrolysis by salivary alpha-amylase is more sensitive to the concentration of sodium azide than is the hydrolysis rate by pancreatic alpha-amylase. At this concentration of sodium azide, the molar extinction coefficient of the chromogen was not effected.

EXAMPLE 15

Amylase Assay with 4-Chloro-2-nitro-1-naphthyl-alphamaltotrioside

Using the same pH 6 assay buffer of Example 14, 4-chloro-2-nitro-1-naphthyl-alpha-maltotrioside of Example 3 was dissolved at a concentration of 2.0 mg/ml (2.77 mM). The change in absorbance at 450 nm (i.e. maximum for free chromogen) was monitored at 37° C. on a Gilford spectrophotometer after addition of 100 ul control serum containing 478 U/L of pancreatic amylase. Over a linear interval of 0.5 min to 6.0 min, a $\Delta A_{450}$/min of 0.0293 was recorded.

EXAMPLE 16

End-point alpha-Amylase Assay—Comparison of 2-Chloro-4-nitrophenyl-alpha-maltotrioside with 4-Nitrophenyl-alpha-maltotrioside A direct comparison was made between the 2-chloro-4-nitrophenyl-alpha-maltotrioside of the instant invention with the known alpha-amylase substrate, 4-nitrophenyl-alpha-maltotrioside in the following manner:

2-Chloro-4-nitrophenyl-alpha-maltotrioside and 4-nitrophenyl-alpha-maltotrioside were each dissolved at a 4-nitrophenyl-alpha concentration of 4 mg/ml in 2.0 ml of the pH 6 assay buffer of Example 13, and 1 mg/ml sodium azide preservative. The sample solutions were each warmed to 37° C. and 100 ul of human pancreatic alpha-amylase control serum containing 428 U/ml was added to each solution. At the end of 10 minutes, the solutions were each diluted with 2.0 ml of stopping reagent to bring the pH to 10.15. Reagent blanks without added amylase were likewise treated. The absorbance at 405 nm was immediately recorded and the $\Delta A_{405}$ between sample solutions and reagent blank was calculated. For the 2-chloro-4-nitrophenyl-alpha-maltotrioside sample, a $\Delta A_{405}$ of 0.561 was realized which corresponds to $13.5 \times 10^{-2}$ u moles of released chromogen based upon a millimolar extinction of 16.60 for free chromogen at 405 nm and pH 10.15. On the other hand, the 4-nitrophenyl-alpha-maltotrioside sample gave a $\Delta A_{405}$ of 0.061 which corresponds to $1.30 \times 10^{-2}$ u moles of released chromogen based upon a millimolar extinction at 405 nm and pH 10.15 of 18.80. Thus the 2-chloro-4-nitrophenyl-alpha maltotrioside is hydrolyzed ten times faster than 4-nitrophenyl-alpha-maltotrioside.

The spectral properties of several of the chromogens of the instant invention were compared to monosubstituted nitrophenols in terms of the molar extinction coefficients at the optimum pH for amylase assay, the results, as shown in the Table below, indicate improved spectral properties for the chromogens of the instant invention.

TABLE

| Chromogen | Absorbance Maximum (nm) (Amax) at pH 6 | Molar Extinction Coefficient at pH 6 (Emax) L Mol$^{-1}$ cm$^{-1}$ |
| --- | --- | --- |
| p-nitrophenol | 405 | 1,500 |
| o-nitrophenol | 405 | 750 |
| 2-chloro-4-nitrophenol | 398 | 13,107 |
| 2-formyl-4-nitrophenol | 385 | 11,854 |
| 2-nitro-4-chloro-1-naphthol | 450 | 8,326 |

We claim:

1. A direct method for determining the alpha-amylase content of a sample containing alpha-amylase which comprise (a) adding a a reagent system for alpha-amylase which comprises an aromatic substituted glycoside substrate for alpha-amylase of the formula,

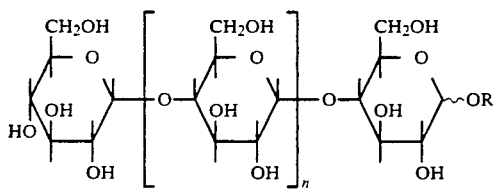

wherein the substitutent —OR is cleavable therefrom to form a chromophore and wherein the configuration of the substituent —OR on the anomeric carbon is alpha-, n is an integer of 0 or 1, and R is a substituted aromatic selected from the group consisting of

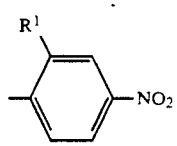

(a')

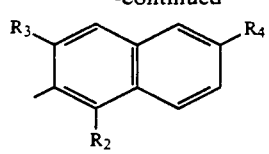

(b')

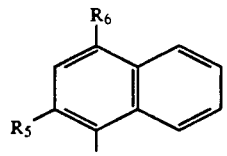

(c')

where $R_1$ through $R_6$ are independently halogen, $NO_2$,-$SO_3H$,

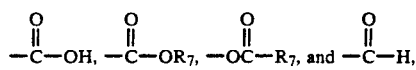

where $R_7$ is loweralkyl; a buffer, and an effective amount of an enzyme activator selected from the group consisting of hydroazoic acid, an alkali metal azide and an alkaline earth azide to a measured quantity of the sample to react the alpha-amylase contained in the sample with said aromatic substituted glycoside substrate to cleave the —OR substituent to form said chromophore; (b) monitoring the the absorbance of said formed chromophore; and (c) relating the alpha-amylase content of the sample to the absorbance of the chromophore.

2. A method as defined in claim 1 wherein n is 1 and R of said compound is (a').

3. The method as defined in claim 2 wherein $R_1$ is chloro.

4. The method as defined in claim 1 wherein the alkali metal azide is sodium azide.

5. The method as defined in claim 1 wherein the alkali metal azide is lithium azide.

6. The method as defined in claim 4 wherein the maximum absorbance of the chromophore is monitored.

* * * * *